(12) United States Patent
Reimers et al.

(10) Patent No.: US 12,171,441 B2
(45) Date of Patent: Dec. 24, 2024

(54) BONE MARROW HARVESTING AND STORAGE

(71) Applicant: Stryker European Operations Holdings LLC, Kalamazoo, MI (US)

(72) Inventors: Nils Reimers, Kiel (DE); Robin Büscher, Heikendorf (DE)

(73) Assignee: Stryker European Operations Holdings LLC, Portage, MI (US)

( * ) Notice: Subject to any disclaimer, the term of this patent is extended or adjusted under 35 U.S.C. 154(b) by 1632 days.

(21) Appl. No.: 16/199,963

(22) Filed: Nov. 26, 2018

(65) Prior Publication Data

US 2019/0090889 A1 Mar. 28, 2019

Related U.S. Application Data

(63) Continuation of application No. 14/616,071, filed on Feb. 6, 2015, now abandoned.
(Continued)

(51) Int. Cl.
*A61B 17/16* (2006.01)
*A61F 2/46* (2006.01)
(Continued)

(52) U.S. Cl.
CPC ........ *A61B 17/1635* (2013.01); *A61F 2/4644* (2013.01); *A61K 35/28* (2013.01);
(Continued)

(58) Field of Classification Search
None
See application file for complete search history.

(56) References Cited

U.S. PATENT DOCUMENTS 5,694,951 A 12/1997 Bonutti
5,993,387 A * 11/1999 Moore .................. G16H 70/20
600/300
(Continued)

FOREIGN PATENT DOCUMENTS

CN 1432645 A 7/2003

OTHER PUBLICATIONS

Porter et al. "Osteogenic Potential of Reamer Irrigator Aspirator (RIA) Aspirate Collected from Patients Undergoing Hip Arthroplasty". J Orthop Res. Jan. 2009 ; 27(1): 42-49. 2009 (Year: 2009).*
(Continued)

*Primary Examiner* — Jonathan Ng
(74) *Attorney, Agent, or Firm* — Lerner David LLP

(57) ABSTRACT

Methods of extracting bone and/or cellular material from a patient for possible use in a later surgical procedure, which involves that patient or even a different patient, are provided. An embodiment of the method generally comprises extracting bone and/or cellular material from a patient undergoing a routine surgical procedure, saving the material, and then sending it to a storage, separation, and processing facility (e.g., a "biobank") for use in a later surgical procedure involving that patient, or a different patient. The material may be cancellous bone, cortical bone chips, or bone marrow. The extracted bone and/or cellular material can be processed at the biobank and used in a multitude of different medical procedures (e.g., as an allograft infused with stem cells for use in a fusion procedure).

13 Claims, 1 Drawing Sheet

Related U.S. Application Data

(60) Provisional application No. 61/936,590, filed on Feb. 6, 2014.

(51) Int. Cl.
  *A61K 35/28* (2015.01)
  *A61K 35/32* (2015.01)
  *A61M 1/00* (2006.01)
  *G16H 10/40* (2018.01)
  *A61F 2/28* (2006.01)
  *A61K 35/12* (2015.01)

(52) U.S. Cl.
  CPC ............ *A61K 35/32* (2013.01); *A61M 1/774* (2021.05); *G16H 10/40* (2018.01); *A61B 2217/005* (2013.01); *A61B 2217/007* (2013.01); *A61F 2002/2835* (2013.01); *A61K 2035/122* (2013.01); *A61K 2035/124* (2013.01); *A61M 2202/10* (2013.01); *A61M 2205/52* (2013.01)

(56) References Cited

U.S. PATENT DOCUMENTS

| | | | |
|---|---|---|---|
| 6,022,354 | A | 2/2000 | Mercuri et al. |
| 6,071,284 | A | 6/2000 | Fox |
| 6,139,509 | A | 10/2000 | Yuan et al. |
| 6,325,806 | B1 | 12/2001 | Fox |
| 6,332,886 | B1 | 12/2001 | Green et al. |
| 6,387,070 | B1 | 5/2002 | Marino et al. |
| 6,440,138 | B1 | 8/2002 | Reiley et al. |
| 6,783,533 | B2 | 8/2004 | Green et al. |
| 8,038,679 | B2 | 10/2011 | Wieland |
| 8,425,518 | B2 | 4/2013 | Wieland |
| 2002/0099401 | A1 | 7/2002 | Bonutti |
| 2005/0010437 | A1* | 1/2005 | Abukwedar ........... G16H 70/20 705/2 |
| 2008/0177200 | A1 | 7/2008 | Ikehara et al. |
| 2008/0189045 | A1* | 8/2008 | Moore ................... G16H 10/40 702/19 |
| 2008/0195105 | A1 | 8/2008 | Sidebotham et al. |
| 2008/0215364 | A1 | 9/2008 | Brevnova et al. |
| 2009/0053282 | A1 | 2/2009 | Smiler et al. |
| 2009/0138354 | A1* | 5/2009 | Zech ....................... G16H 70/60 705/14.17 |
| 2010/0298835 | A1 | 11/2010 | Ralph et al. |
| 2011/0054929 | A1* | 3/2011 | Centeno ................. G06Q 30/08 705/2 |
| 2011/0262405 | A1 | 10/2011 | Segina et al. |
| 2012/0052049 | A1 | 3/2012 | Woods et al. |
| 2013/0052169 | A1 | 2/2013 | Marom |
| 2013/0253519 | A1 | 9/2013 | Mitchell et al. |
| 2015/0193581 | A1 | 7/2015 | Kaminski et al. |
| 2015/0216539 | A1 | 8/2015 | Reimers et al. |

OTHER PUBLICATIONS

Extended European Search Report and Written Opinion for EP Application No. 15705463.6, dated Aug. 28, 2018.
G. Cox et al., The use of the reamer-irrigator-aspirator to harvest mesenchymal stem cells, J Bone Joint Surg [Br];93-3:517-24, 2011.
International Search Report and Written Opinion for Application No. PCT/US2015/014814 dated Apr. 9, 2015.
Nielsen, et al., "Bone Bank Service in Odense, Denmark. Audit of the First Ten Years with Bone Banking at the Department of Orthopaedics, Odense University Hospital", vol. 2, No. 3, Cell and Tissue Banking, Sep. 2001, pp. 179-183.
Perry et al., "Collection, Cryopreservation, and Characterization of Human Dental Pulp-Derived Mesenchymal Stem Cells for Banking and Clinical Use", Tissue Engineering: Part C, vol. 14, No. 2, 2008.
Sterigraft, Bone Bank Allografts, website printout, Jan. 23, 2014.

* cited by examiner

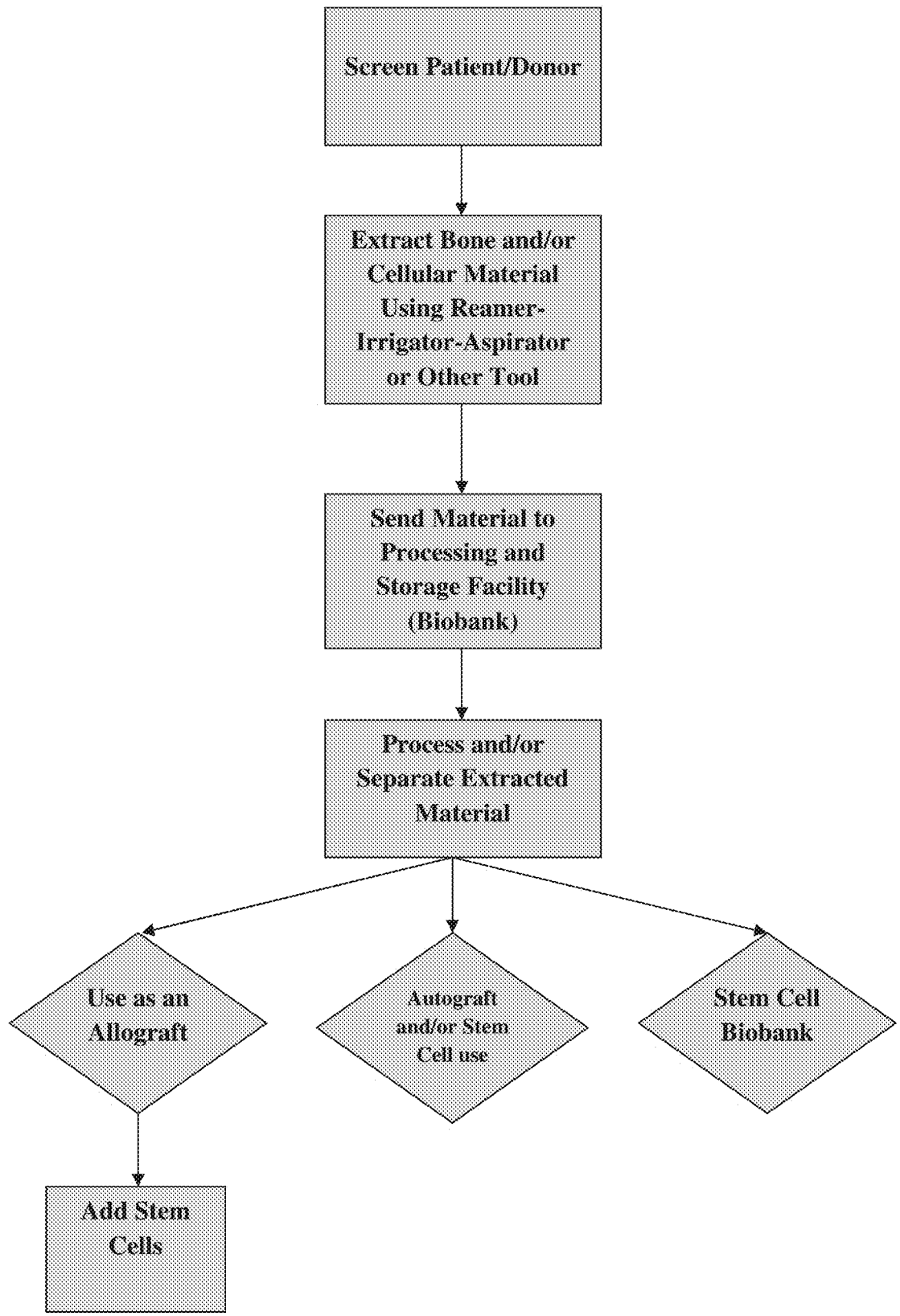

BONE MARROW HARVESTING AND STORAGE

CROSS-REFERENCE TO RELATED APPLICATIONS

This application is a continuation of U.S. application Ser. No. 14/616,071, filed on Feb. 6, 2015, which claims the benefit of the filing date of U.S. Provisional Application No. 61/936,590, filed Feb. 6, 2014, the disclosures of which are hereby incorporated by referenced herein.

BACKGROUND OF THE INVENTION

The present invention relates to methods of harvesting and processing bone and/or cellular material for use in various medical treatments.

Pseudarthrosis, also referred to as non-union of bone, is a common issue surrounding fracture treatment. Non-union occurs when a particular patient's fracture site fails to heal within a specified period of time, and thus requires some sort of intervention (e.g., surgical) in order to achieve proper union and mobility. In some cases, non-unions may be treated by bone grafting (e.g., allograft, autograft, or xenograft), through internal or external fixation, or a combination thereof. Bone grafting offers an opportunity to stimulate the fracture site so that bony formation occurs at the site, thereby causing proper union of the fracture.

Stem cells (e.g., Mesenchymal stem cells (MSCs), Hematopoietic stem cells (HSCs), or other stem cells) are known to be useful with certain graft materials, or by themselves, to facilitate bone growth and formation when used appropriately. For example, adult MSCs are capable of differentiating into a variety of different cell types including osteoblasts (bone cells), chondrocytes (cartilage cells), and adipocytes (fat cells). As such, when incorporated with certain allograft material, stem cells can assist with the proper formation of bone and union of bone parts at a fracture site. In many cases, however, stem cells of the type discussed above must first be extracted from a patient and processed before use. As an example, extracted bone marrow of a patient can provide the necessary stem cells. However, the bone marrow is typically extracted in a multi-staged procedure. In a first stage of the procedure, bone marrow is aspirated from a patient (e.g., at the iliac crest) and then sent to a laboratory for processing. It is only then, in a second stage of the procedure, that the bone marrow previously harvested and processed may be used for the patient's particular application. Thus, a patient must undergo multiple surgical operations in order to acquire the necessary stem cells.

BRIEF SUMMARY OF THE INVENTION

The present invention seeks to provide novel methods of harvesting, processing, and storing bone and/or cellular material (e.g., cancellous bone, bone chips, bone marrow, and stem cells) for use in various medical applications.

A first aspect of the invention includes a method of harvesting and processing bone and/or cellular material. The method comprises reaming bone with a tool to extract cancellous bone, cortical bone chips, and/or bone marrow material during an orthopedic procedure, transferring the extracted material to a container fluidly connected with the tool, sending the extracted material to a facility, and processing, separating, and/or storing the extracted material at the facility so that the material is usable as at least one of: (1) an allograft infused with stem cells; (2) an autograft with or without stem cells infused; and (3) stem cells. The surgical procedure undergone is a procedure conducted in the ordinary course of events and is not a surgery dedicated predominantly to extracting the cancellous bone, cortical bone chips, and/or bone marrow material. In other words, it is a commonly-conducted surgical procedure not exclusively dedicated to the extraction of the cancellous bone, cortical bone chips, and/or bone marrow material. The method according to this first aspect may also comprise the step of extracting the cancellous bone, cortical bone chips, and/or bone marrow material using a reamer-irrigator-aspirator.

A second aspect of the invention includes a method of processing, separating, and/or storing bone or cellular material. The method comprises: (1) identifying a set of patients undergoing an existing surgical operation in which a bone of the patient is to be reamed or resected and cancellous bone, cortical bone chips, and/or bone marrow material removed, (2) screening the patients using a set of criteria to ascertain a subset of patients who qualify to donate cancellous bone, cortical bone chips, and/or bone marrow, wherein a first aspect of the criteria requires the patient to be undergoing an existing operation in the ordinary course of events, which is not a surgery dedicated predominantly to extracting the cancellous bone, cortical bone chips, and/or bone marrow material, (3) instructing a controlling entity for the surgical operation to send the extracted cancellous bone, cortical bone chips, and/or bone marrow material to a processing, separation, and storage facility, and (4) processing, separating, and/or storing the cancellous bone, cortical bone chips, and/or bone marrow material so that the material is usable as at least one of: (a) an allograft infused with stem cells; (b) an autograft with or without stem cells infused; and (c) stem cells. The method according to this second aspect may also comprise the step of instructing the controlling entity to save and not discard the extracted cancellous bone, cortical bone chips, and/or bone marrow material, wherein typical practice for the controlling entity is to discard such material.

A third aspect of the invention includes a method of processing, separating, and/or storing bone or cellular material. The method comprises: (1) identifying a set of patients undergoing an existing surgical operation in which cancellous bone, cortical bone chips, and/or bone marrow material is to be removed from the patient; (2) screening the patients using a set of criteria to ascertain a subset of patients who qualify to donate the cancellous bone, cortical bone chips, and/or bone marrow material, wherein a first aspect of the criteria requires the patient to be undergoing an existing operation in the ordinary course of events, which is not a surgery dedicated predominantly to extracting the cancellous bone, cortical bone chips, and/or bone marrow material; (3) obtaining and saving the extracted cancellous bone, cortical bone chips, and/or bone marrow material resulting from the surgical operation, wherein the cancellous bone, cortical bone chips, and/or bone marrow material would have otherwise been discarded after the surgical operation; and (4) sending the cancellous bone, cortical bone chips, and/or bone marrow material to a processing, separation, and storage facility for processing, separating, and/or storing the cancellous bone, cortical bone chips, and/or bone marrow material so that the material is usable as at least one of: (a) an allograft infused with stem cells; (b) an autograft with or without stem cells infused; and (c) stem cells. In an embodiment of this third aspect, the cancellous bone, cortical bone chips, and/or bone marrow material, after processing and/or separation, is stored as stem cells in a biobank.

BRIEF DESCRIPTION OF THE DRAWINGS

A more complete appreciation of the subject matter of the present invention and of the various advantages thereof can be realized by reference to the following detailed description in which reference is made to the accompanying drawings in which:

FIG. 1 is a flowchart demonstrating an embodiment of the method disclosed herein.

DETAILED DESCRIPTION

In describing particular embodiments of the present invention, specific terminology will be used for the sake of clarity. However, the invention is not intended to be limited to any specific terms used herein, and it is to be understood that each specific term includes all technical equivalents, which operate in a similar manner to accomplish a similar purpose.

As used herein, the phrase bone and/or cellular material refers to material that is extractable from bone, which optionally may be processed and/or separated to produce another material. For instance, bone and/or cellular material may include cancellous bone, cortical bone (in the form of chips or morselized bone), bone marrow material, or stem cells produced from any of the foregoing materials. Such materials frequently are found, for example, in the medullary canal (as well as the bone surrounding the canal) of a long bone.

The present invention involves a method of extracting bone and/or cellular material from a patient for possible use in a later surgical procedure, which involves that patient or even a different patient. The method generally comprises extracting bone and/or cellular material from a patient undergoing a routine surgical procedure, saving the material, and then sending it to a storage, separation, and processing facility (e.g., a "biobank") for use in a later surgical procedure involving that patient, or a different patient. The extracted bone and/or cellular material can be processed at the biobank and used in a multitude of different medical procedures, as set forth in more detail below.

Bone and/or cellular material may be extracted from a patient during a procedure that involves resection of bone, reaming of a medullary canal of bone, or both. A substantial amount of reaming and/or resection of bone occurs in a variety of surgical procedures conducted daily all over the world, such as in intramedullary nailing (IM nail) procedures, in hip replacements, during knee revisions, or even still other procedures. Using IM nail procedures as an example, a surgeon seeking to remedy a fracture in a long bone (e.g., a fracture in the tibia) typically first makes an incision in the patient's skin adjacent the knee. A K-wire can then be inserted through the patient's skin and into an entry point on the patient's tibial plateau. In a reamed technique, the surgeon then uses the K-wire to guide a reamer through the entry point and into the medullary canal of the long bone. With the K-wire extending within the long bone and past the fracture site (e.g., so that the fracture can be properly reduced), one or more reamers may then be used sequentially to remove cortical and cancellous bone, as well as bone marrow material from the patient. Frequently, final reaming is larger than the diameter of the IM nail to be used (and also the medullary canal of the bone). The cortical, cancellous, and bone marrow material extracted during the aforementioned reaming procedure is oftentimes discarded. Using the method contemplated herein, however, those materials may be saved for processing, separation, and/or storage so that the materials can be reused in a variety of ways.

In the method disclosed herein, the bone and/or cellular material extracted from a patient undergoing a routine procedure, as detailed above (e.g., an IM nail procedure), is sent to a biobank facility instead of being discarded, as in the current practice. FIG. 1 reflects an embodiment of this method. For instance, as shown in step 1 of FIG. 1, the method may comprise first determining the eligibility of patients/donors by screening all possible patients/donors and then filtering out a certain subset according to particular criteria (e.g., the screening being conducted by the hospital or possibly the biobank). The criteria may take into account the age of a patient, the quality of the patient's bone and/or cellular material, the patient's fitness or lifestyle, or other relevant criteria. If a particular patient meets the set criteria, he/she may be selected as a possible donor of material.

As reflected in FIG. 1, after the screening process the bone and/or cellular material may be extracted from the qualified patient/donor. In one embodiment, such as in IM nail procedures, a dedicated tool may be used to extract the material.

The dedicated tool for extraction of bone and/or cellular material is, in a particular embodiment, a reamer-irrigator-aspirator (RIA) (not shown). The RIA may include a reaming end that is fluted or otherwise shaped to be able to dig into bone and ream out the medullary canal of a long bone (e.g. the tibia). The RIA may be powered or non-powered (manual). In certain embodiments, the RIA is also cannulated so as to direct cancellous bone material, cortical bone chips, and/or bone marrow through the RIA and to a container for holding the material. Multiple apertures leading into the aspiration cannula of the RIA can be provided (e.g., at the reaming end of the RIA), or the RIA could include multiple apertures leading to multiple cannulations for extracting and transferring the aforementioned material to the container. In an embodiment, the container may comprise separate individual containers for different uses of the bone and/or cellular material. As an example, the container may comprise three (3) individual containers, a first container for typification of the donor (e.g., to determine blood type, etc.), a second container for safety/quality examination, and a third main container for storage of the bone and/or cellular material (e.g., stem cells) for later use with that patient, or a different patient. In this way, the RIA can provide a convenient means of accumulating all the necessary materials needed for proper banking of the bone and/or cellular material for later use. In one embodiment, the three (3) separate containers are initially joined together, but can be detached and used for their separate purposes, as described above.

A separate irrigation port and canal may also extend within the RIA for providing irrigation during the procedure, and an aperture may be positioned at the reaming end of the RIA for releasing irrigation fluid at the reaming end. In some instances, a conduit is fluidly connected with the aspiration cannula and the container so that the extracted material can travel from the medullary canal, through the RIA, into the conduit, and finally to the container. A separate conduit may also be fluidly connected with the irrigation canal to allow fluid to travel through the conduit, into the irrigation canal, to the reaming end, and out of the aperture positioned at the reaming end. This provides irrigation at the reaming end of the RIA. Because of the above-described features, the RIA is configured to ream the medullary canal of a bone, extract cancellous, cortical, and bone marrow material from the bone, and also provide irrigation to assist with the reaming process and provide smooth operation.

In an optional embodiment, the RIA also includes a filter positioned in fluid communication with the container so that the material being extracted from the patient/donor can be filtered, as necessary. The filter allows the RIA to extract material that only meets certain defined criteria (e.g., particular sized bone chips, morsels, and/or marrow). A vacuum source can also be fluidly connected to the RIA (e.g., to an end of the filter, to the aspiration cannula, or to another section of the RIA) for providing negative pressure in the medullary canal. The negative pressure, in combination with irrigation, causes the cancellous bone, cortical bone chips, and bone marrow to travel through the aspiration cannula and to the container. If a filter is included, the negative pressure also causes the aforementioned materials to pass through the filter. An example of a RIA can be found in U.S. Patent Pub. No. 2011/0262405, titled "Apparatus, System, and Method for Harvesting Improved Bone Graft Material with Reamer-Irrigator-Aspirator (RIA) Device," which is hereby incorporated by reference herein. The RIA taught in the '405 publication is usable in any of the methods disclosed herein.

Referring again to FIG. 1, after extracting the bone and/or cellular material from the patient, either by using the RIA or another tool for extraction, the extracted material may then be sent to the storage and processing facility/biobank. It is not discarded, as is the case with many IM nail or other like procedures conducted currently. Additionally, if separate containers are used, the other containers can be used for typification of the donator and/or for safety examination of the extracted material. Once at the biobank, the extracted cancellous bone, cortical bone chips, and/or bone marrow may be processed or separated for use in a variety of different procedures. For instance, as reflected in FIG. 1, the extracted material may be stored at the biobank for use as an allograft. Optionally, the allograft material can be infused with stem cells from the material collected during the surgical procedure. For instance, stem cells may be separated from the bone marrow material extracted from the patient/donor, and infused into the cancellous bone and/or bone chips to construct an allograft containing stem cells. The stem cells act to vastly improve the allograft material because of the cells' ability to differentiate into several different cell types (e.g., osteoblasts for bone formation, chondrocytes for cartilage formation, and adipocytes for formation of fat cells). As such, with the allograft material infused with stem cells, it can act as a fusion material for use in better remedying fracture sites or in other bone fusion procedures (e.g., fusion procedures in the spine). The allograft thusly acts more like an autograft due to its improved characteristics, and may be stored at the biobank for use by another qualifying patient in a future procedure.

Another application for the extracted cancellous bone, bone chips, and/or bone marrow material is for use as an autograft for the same patient/donor. In particular, the patient/donor may elect to pay a certain storage and processing fee to the biobank for holding the patient's extracted material so that the material is available for possible use at a later date. In this scenario, the autograft material may or may not be infused with stem cells, as detailed above. Alternatively, the patient may elect to simply have his/her stem cells processed at the biobank (e.g., from the extracted bone marrow material) so that those cells are available for future use in a variety of ways. The stem cells could be used in autograft applications, as noted above, or for treating leukemia, aplastic anemia, or other diseases of the immune system. The stem cells stored by the patient can therefore provide a significant benefit to the patient or his/her relatives, if needed at some future point. Further, since the patient has already stored his/her stem cells after a previously-conducted surgical procedure, which would have been undertaken regardless, the patient does not have to have multiple surgeries in order to obtain the necessary stem cells/material. In other words, in a typical scenario a patient needing stem cell material would first have to extract the material through a surgical procedure (e.g., from the iliac crest). The stem cell material would then be processed, and only weeks later could it be used by the patient in the particular treatment being administered. However, if that patient previously stored his/her stem cell material after a different surgery (e.g., an IM nail procedure) at the biobank, the stem cell material would immediately be available for use and the patient would not require a separate surgery to extract the material.

Yet another application for the extracted bone and/or cellular material may be to maintain a stem cell biobank, as set forth in FIG. 1. As an example, after extraction of bone and/or cellular material as set forth above, the bone and/or cellular material may be sent to a biobank facility where it can be processed and separated, if necessary. This material may come from the third, main container of the RIA described above. Any stem cells in the material (e.g., extracted bone marrow) can also be cultured and stored at the biobank for use by the patient/donor, or by another patient. The stem cells can be used for a vast variety of procedures, such as those detailed above or otherwise known in the art. A registry can be maintained in which the stem cells are categorized for use by the patient/donor or another patient. Thus, a greater availability of stem cells would be present than is currently the case. This is due to the fact that the stem cells are harvested as a result of surgical procedures conducted quite frequently throughout the world.

An advantage of the above-described method and uses for extracted bone and/or cellular material is that the material is extracted from patients undergoing commonly-conducted surgeries. A large volume of material can therefore be gathered worldwide. In addition, this material is typically discarded or not used in the manner set forth herein. The disclosed method could therefore allow surgeons and hospitals to collect the material, with patient consent of course, and send the material to the biobank for processing, separation, and/or storage so that the material is usable in the manner discussed.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of processing, separating, and storing extracted bone or cellular material comprising:
   identifying a set of patients undergoing an existing surgical operation in which a bone of the patient is to be reamed or resected and cancellous bone, cortical bone chips, and bone marrow material removed;
   screening the patients using a set of criteria to ascertain a subset of patients who qualify to donate cancellous bone, cortical bone chips, and bone marrow, wherein a first aspect of the criteria requires the patient to be undergoing an existing operation in the ordinary course of events, which is not a surgery dedicated predominantly to extracting the cancellous bone, cortical bone chips, and bone marrow material;

extracting cancellous bone, cortical bone chips, and bone marrow from the subset of patients using a reamer-irrigator-aspirator;

instructing a controlling entity for the surgical operation to send the extracted cancellous bone, cortical bone chips, and bone marrow material to a processing, separation, and storage facility; and processing, separating, and storing the cancellous bone, cortical bone chips, and bone marrow material, by the processing, separation, and storage facility, so that the material is usable as at least one of: (1) an allograft infused with stem cells; (2) an autograft with or without stem cells infused; and (3) stem cells.

2. The method according to claim 1, wherein the criteria used for screening also involves considering the patient's age, health, and quality of the extracted cancellous bone, cortical bone chips, and bone marrow material being donated.

3. The method according to claim 1, further comprising the step of maintaining a stem cell biobank using at least one of the extracted cancellous bone, cortical bone chips, and bone marrow material.

4. The method according to claim 2, further comprising the step of supplying stem cells to qualifying patients in need after the processing, separating, or storing step.

5. The method according to claim 1, further comprising the step of instructing the controlling entity to save and not discard the extracted cancellous bone, cortical bone chips, and bone marrow material, wherein typical practice for the controlling entity is to discard such material.

6. The method according to claim 1, further comprising the step of accepting payment from the screened patient or patients to store and/or process their extracted cancellous bone, cortical bone chips, and bone marrow material for future use.

7. The method according to claim 1, wherein the cancellous bone, cortical bone chips, and bone marrow material, after processing and/or separation, is stored as stem cells in a biobank.

8. A method of processing, separating, and storing extracted bone or cellular material comprising:

identifying a set of patients undergoing an existing surgical operation in which cancellous bone, cortical bone chips, and bone marrow material is to be removed from the patient;

screening the patients using a set of criteria to ascertain a subset of patients who qualify to donate the cancellous bone, cortical bone chips, and bone marrow material, wherein a first aspect of the criteria requires the patient to be undergoing an existing operation in the ordinary course of events, which is not a surgery dedicated predominantly to extracting the cancellous bone, cortical bone chips, and bone marrow material;

extracting cancellous bone, cortical bone chips, and bone marrow from the subset of patients using a reamer-irrigator-aspirator;

obtaining and saving the extracted cancellous bone, cortical bone chips, and bone marrow material resulting from the surgical operation, wherein the cancellous bone, cortical bone chips, and bone marrow material would have otherwise been discarded after the surgical operation; and sending the cancellous bone, cortical bone chips, and bone marrow material to a processing, separation, and storage facility for processing, separating, and storing the cancellous bone, cortical bone chips, and bone marrow material so that the material is usable as at least one of: (1) an allograft infused with stem cells; (2) an autograft with or without stem cells infused; and (3) stem cells.

9. The method according to claim 8, wherein the cancellous bone, cortical bone chips, and bone marrow material, after processing and/or separation, is stored as stem cells in a biobank.

10. The method according to claim 9, further comprising establishing a registry categorizing the stem cells for future use by the patient or another patient.

11. The method according to claim 10, further comprising identifying a second patient as a candidate for benefiting from use of the patient's stem cells using the registry, and supplying the second patient with such cells for use in a surgical operation.

12. The method according to claim 8, wherein the criteria used for screening also involves considering the patient's age, health, and/or quality of the extracted cancellous bone, cortical bone chips, and bone marrow material being donated.

13. The method according to claim 8, wherein the surgical operation is an orthopedic operation involving reaming of a bone of the patient, in particular a medullary canal of the bone.

* * * * *